US012673083B2

(12) United States Patent
Tharaux et al.

(10) Patent No.: US 12,673,083 B2
(45) Date of Patent: Jul. 7, 2026

(54) TREM-1 INHIBITORS FOR THE TREATMENT OF VASO-OCCLUSIONS AND TISSUE INJURIES IN PATIENTS SUFFERING FROM SICKLE CELL DISEASE

(71) Applicants: INSERM (INSTITUT NATIONAL DE LA SANTÉ ET DE LA RECHERCHE MÉDICALE), Paris (FR); UNIVERSITÉ PARIS CITÉ, Paris (FR); INOTREM, Paris (FR)

(72) Inventors: Pierre-Louis Tharaux, Paris (FR); Olivia Lenoir, Paris (FR); Thomas Mintz, Paris (FR)

(73) Assignees: INSERM (INSTITUT NATIONAL DE LA SANTÉ ET DE LA RECHERCHE MÉDICALE, Paris (FR); UNIVERSITÉ DE PARIS, Paris (FR); INOTREM, Paris (FR)

( * ) Notice: Subject to any disclaimer, the term of this patent is extended or adjusted under 35 U.S.C. 154(b) by 1061 days.

(21) Appl. No.: 17/778,571

(22) PCT Filed: Nov. 24, 2020

(86) PCT No.: PCT/EP2020/083241
§ 371 (c)(1),
(2) Date: May 20, 2022

(87) PCT Pub. No.: WO2021/105137
PCT Pub. Date: Jun. 3, 2021

(65) Prior Publication Data
US 2023/0016187 A1     Jan. 19, 2023

(30) Foreign Application Priority Data
Nov. 25, 2019     (EP) .................................... 19306520

(51) Int. Cl.
*A61K 38/04*          (2006.01)
*A61P 7/00*           (2006.01)
(52) U.S. Cl.
CPC ............... *A61K 38/04* (2013.01); *A61P 7/00* (2018.01)
(58) Field of Classification Search
CPC . A61K 38/00; A61K 38/04; A61P 7/00; A61P 7/02
See application file for complete search history.

(56) References Cited

U.S. PATENT DOCUMENTS

2015/0232531 A1     8/2015  Gibot

FOREIGN PATENT DOCUMENTS

| EP | 2 835 641 A1 | 2/2015 |
| WO | 2004/01333 A2 | 2/2004 |
| WO | 2012/120130 A1 | 9/2012 |
| WO | 2015/165944 A1 | 11/2015 |
| WO | 2019/057972 A1 | 3/2019 |

OTHER PUBLICATIONS

Washington et al: A Trem family member, TLT-1, is found exclusively in the alpha-granules of megakaryocytes and platelets, Blood, vol. 104, No. 4, p. 1042-1047, Aug. 15, 2004.

*Primary Examiner* — D. L. Jones
(74) *Attorney, Agent, or Firm* — WCF IP

(57) ABSTRACT

Sickle cell disease (SCD) is a single gene disorder characterized by mutant hemoglobin-S (HbS) and chronic intravascular haemolysis. Painful vaso-occlusive crises (VOC) are typical of SCD and often associated to a further rise in hemolysis. VOC is the clinically painful form of vaso-occlusion, that is due to the aggregation of red blood cells in the capillaries and venules. Such event is promoted or aggravated by adhesion of polymorphonuclear neutrophils (PMNs) to red blood cells and the endothelium leading to tissue ischemia, inflammation and imperfect repair. Repeated vaso-occlusion and PMNs interactions with the vascular endothelium are thought to promote microvascular injuries in SCD patients. The inventors tested the effect of pharmacological inhibition of TREM-1 with LR12 peptide in two experimental vaso-occlusive crisis models. Additional validation of TREM-1 involvement in vaso-occlusion was verified using mice with sickle cell disease and Trem-1 gene deficiency. In particular, the inventors showed that TREM-1 inhibition is particular suitable for limiting the severity of vaso-occlusions. The results obtained by the inventors also suggest that plasmatic concentration of sTREM-1 could be a reliable biomarker for predicting vaso-occlusions and/or SCD-associated organ dysfunction and end-organ damage.

1 Claim, 7 Drawing Sheets

Specification includes a Sequence Listing.

Ter-119 positive area (%)

A

B

TREM-1 antagonism blunts neutrophils infiltrates in tissues upon VOC in SS mice

SEQUENCE LISTING

```
<160> NUMBER OF SEQ ID NOS: 12

<210> SEQ ID NO 1
<211> LENGTH: 234
<212> TYPE: PRT
<213> ORGANISM: Homo sapiens

<400> SEQUENCE: 1

Met Arg Lys Thr Arg Leu Trp Gly Leu Leu Trp Met Leu Phe Val Ser
1               5                   10                  15

Glu Leu Arg Ala Ala Thr Lys Leu Thr Glu Glu Lys Tyr Glu Leu Lys
            20                  25                  30

Glu Gly Gln Thr Leu Asp Val Lys Cys Asp Tyr Thr Leu Glu Lys Phe
        35                  40                  45

Ala Ser Ser Gln Lys Ala Trp Gln Ile Ile Arg Asp Gly Glu Met Pro
    50                  55                  60

Lys Thr Leu Ala Cys Thr Glu Arg Pro Ser Lys Asn Ser His Pro Val
65                  70                  75                  80

Gln Val Gly Arg Ile Ile Leu Glu Asp Tyr His Asp His Gly Leu Leu
                85                  90                  95

Arg Val Arg Met Val Asn Leu Gln Val Glu Asp Ser Gly Leu Tyr Gln
            100                 105                 110

Cys Val Ile Tyr Gln Pro Pro Lys Glu Pro His Met Leu Phe Asp Arg
            115                 120                 125

Ile Arg Leu Val Val Thr Lys Gly Phe Ser Gly Thr Pro Gly Ser Asn
        130                 135                 140

Glu Asn Ser Thr Gln Asn Val Tyr Lys Ile Pro Pro Thr Thr Thr Lys
145                 150                 155                 160

Ala Leu Cys Pro Leu Tyr Thr Ser Pro Arg Thr Val Thr Gln Ala Pro
                165                 170                 175

Pro Lys Ser Thr Ala Asp Val Ser Thr Pro Asp Ser Glu Ile Asn Leu
            180                 185                 190

Thr Asn Val Thr Asp Ile Ile Arg Val Pro Val Phe Asn Ile Val Ile
            195                 200                 205

Leu Leu Ala Gly Gly Phe Leu Ser Lys Ser Leu Val Phe Ser Val Leu
        210                 215                 220
```

```
Phe Ala Val Thr Leu Arg Ser Phe Val Pro
225                 230

<210> SEQ ID NO 2
<211> LENGTH: 17
<212> TYPE: PRT
<213> ORGANISM: Artificial
<220> FEATURE:
<223> OTHER INFORMATION: Synthetic LR17

<400> SEQUENCE: 2

Leu Gln Glu Glu Asp Ala Gly Glu Tyr Gly Cys Met Val Asp Gly Ala
1               5                   10                  15

Arg

<210> SEQ ID NO 3
<211> LENGTH: 12
<212> TYPE: PRT
<213> ORGANISM: Artificial
<220> FEATURE:
<223> OTHER INFORMATION: Synthetic LR12

<400> SEQUENCE: 3

Leu Gln Glu Glu Asp Ala Gly Glu Tyr Gly Cys Met
1               5                   10

<210> SEQ ID NO 4
<211> LENGTH: 6
<212> TYPE: PRT
<213> ORGANISM: Artificial
<220> FEATURE:
<223> OTHER INFORMATION: Synthetic LR6-1

<400> SEQUENCE: 4

Leu Gln Glu Glu Asp Ala
1               5

<210> SEQ ID NO 5
<211> LENGTH: 6
<212> TYPE: PRT
<213> ORGANISM: Artificial
<220> FEATURE:
<223> OTHER INFORMATION: Synthetic LR6-2

<400> SEQUENCE: 5

Glu Asp Ala Gly Glu Tyr
1               5

<210> SEQ ID NO 6
<211> LENGTH: 6
<212> TYPE: PRT
<213> ORGANISM: Artificial
<220> FEATURE:
<223> OTHER INFORMATION: Synthetic LR6-3

<400> SEQUENCE: 6

Gly Glu Tyr Gly Cys Met
1               5

<210> SEQ ID NO 7
<211> LENGTH: 17
<212> TYPE: PRT
<213> ORGANISM: Artificial
<220> FEATURE:
<223> OTHER INFORMATION: Synthetic LP17

<400> SEQUENCE: 7
```

Leu Gln Val Glu Asp Ser Gly Leu Tyr Gln Cys Val Ile Gln His Pro
1               5                   10                  15

Pro

<210> SEQ ID NO 8
<211> LENGTH: 12
<212> TYPE: PRT
<213> ORGANISM: Artificial
<220> FEATURE:
<223> OTHER INFORMATION: Synthetic LP12

<400> SEQUENCE: 8

Leu Gln Val Glu Asp Ser Gly Leu Tyr Gln Cys Val
1               5                   10

<210> SEQ ID NO 9
<211> LENGTH: 6
<212> TYPE: PRT
<213> ORGANISM: Artificial
<220> FEATURE:
<223> OTHER INFORMATION: Synthetic LP6-1

<400> SEQUENCE: 9

Leu Gln Val Glu Asp Ser
1               5

<210> SEQ ID NO 10
<211> LENGTH: 6
<212> TYPE: PRT
<213> ORGANISM: Artificial
<220> FEATURE:
<223> OTHER INFORMATION: Synthetic LP6-2

<400> SEQUENCE: 10

Glu Asp Ser Gly Leu Tyr
1               5

<210> SEQ ID NO 11
<211> LENGTH: 6
<212> TYPE: PRT
<213> ORGANISM: Artificial
<220> FEATURE:
<223> OTHER INFORMATION: Synthetic LP6-3

<400> SEQUENCE: 11

Gly Leu Tyr Gln Cys Val
1               5

<210> SEQ ID NO 12
<211> LENGTH: 311
<212> TYPE: PRT
<213> ORGANISM: Homo sapiens

<400> SEQUENCE: 12

Met Gly Leu Thr Leu Leu Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
            35                  40                  45

Lys Val Trp Cys Arg Phe Leu Pro Glu Gly Cys Gln Pro Leu Val Ser
        50                  55                  60

Ser Ala Val Asp Arg Arg Ala Pro Ala Gly Arg Arg Thr Phe Leu Thr

-continued

```
65                    70                    75                    80

Asp Leu Gly Gly Gly Leu Leu Gln Val Glu Met Val Thr Leu Gln Glu
                85                    90                    95

Glu Asp Ala Gly Glu Tyr Gly Cys Met Val Asp Gly Ala Arg Gly Pro
               100                   105                   110

Gln Ile Leu His Arg Val Ser Leu Asn Ile Leu Pro Pro Glu Glu Glu
               115                   120                   125

Glu Glu Thr His Lys Ile Gly Ser Leu Ala Glu Asn Ala Phe Ser Asp
       130                   135                   140

Pro Ala Gly Ser Ala Asn Pro Leu Glu Pro Ser Gln Asp Glu Lys Ser
145                   150                   155                   160

Ile Pro Leu Ile Trp Gly Ala Val Leu Leu Val Gly Leu Leu Val Ala
               165                   170                   175

Ala Val Val Leu Phe Ala Val Met Ala Lys Arg Lys Gln Gly Asn Arg
               180                   185                   190

Leu Gly Val Cys Gly Arg Phe Leu Ser Ser Arg Val Ser Gly Met Asn
               195                   200                   205

Pro Ser Ser Val Val His His Val Ser Asp Ser Gly Pro Ala Ala Glu
       210                   215                   220

Leu Pro Leu Asp Val Pro His Ile Arg Leu Asp Ser Pro Pro Ser Phe
225                   230                   235                   240

Asp Asn Thr Thr Tyr Thr Ser Leu Pro Leu Asp Ser Pro Ser Gly Lys
               245                   250                   255

Pro Ser Leu Pro Ala Pro Ser Ser Leu Pro Pro Leu Pro Pro Lys Val
               260                   265                   270

Leu Val Cys Ser Lys Pro Val Thr Tyr Ala Thr Val Ile Phe Pro Gly
               275                   280                   285

Gly Asn Lys Gly Gly Gly Thr Ser Cys Gly Pro Ala Gln Asn Pro Pro
       290                   295                   300

Asn Asn Gln Thr Pro Ser Ser
305                   310
```

TREM-1 INHIBITORS FOR THE TREATMENT OF VASO-OCCLUSIONS AND TISSUE INJURIES IN PATIENTS SUFFERING FROM SICKLE CELL DISEASE

FIELD OF THE INVENTION

The present invention is in the field of medicine, in particular hematology and vascular medicine.

BACKGROUND OF THE INVENTION

Sickle cell disease (SCD) is a single gene disorder characterized by mutant hemoglobinS (HbS) and chronic intravascular haemolysis. Painful vaso-occlusive crises (VOC) are typical of SCD and often associated to a further rise in haemolysis. VOC is the clinically painful form of vaso-occlusion, that is due to the aggregation of red blood cells in the capillaries and venules. Such event is promoted or aggravated by adhesion of polymorphonuclear neutrophils (PMNs) to red blood cells and the endothelium leading to tissue ischemia, inflammation and imperfect repair. Repeated vaso-occlusion and PMNs interactions with the vascular endothelium are also thought to promote microvascular injuries in SCD patients. VOC is usually expressed as acute onset pain, most often in the extremities, chest and back. The treatment considers possible contributing factors, hydration status and pain intensity. Pain management may include the administration of non-steroidal anti-inflammatory drugs and opiates. Prevention of vaso-occlusive crises may require long-term treatment with hydroxyurea or an iterative transfusion program. Pain, which is generally very intense, is the main sign of the attack and requires major analgesics. Depending on the organ affected (rarely in isolation), functional consequences are variable, sometimes followed by sequelae or lethal consequences.

TREM-1 (Triggering receptor expressed on myeloid cells 1) is a membrane receptor whose gene is located on human chromosome 6. It is expressed on the surface of monocytes, granulocytes and neutrophils, possibly other cells and platelets. Inhibitors of TREM-1 have been developed for the treatment of inflammatory diseases, sepsis, myocardial infraction and aneurysm.

SUMMARY OF THE INVENTION

As defined by the claims, the present invention relates to the treatment of vaso-occlusions in patients suffering from sickle cell disease. The present invention further relates to a method of determining whether a patient suffering from sickle cell disease has or is at risk of having vaso-occlusion.

DETAILED DESCRIPTION OF THE INVENTION

Although the primary origin of SCD is a hemoglobin disorder, many types of cells contribute considerably to the pathophysiology of the disease. The adhesion of polymorphonuclear neutrophils (PMNs or neutrophils) to activated endothelium is critical in the pathophysiology of SCD and targeting neutrophils and their interactions with endothelium represents an important opportunity for the development of new therapeutics. The inventors focused on TREM-1 (Triggering receptor expressed on myeloid cells 1), a mediator involved in myeloid cells activation and recruitment in tissues, and investigated the involvement of TREM-1 in the interaction of neutrophils with endothelial cells. The inventors tested the effect of pharmacological inhibition of TREM-1 with LR12 peptide. Additional validation of TREM-1 involvement in vaso-occlusion was verified using mice with sickle cell disease and Trem-1 gene deficiency. They used fluorescence intravital microscopy analyses of the microcirculation in two models of sickle mice enabling pharmacological and genetic alteration of the TREM-1 signaling, and a model of experimental vaso-occlusion. These experiments indicate that blocking the TREM-1 pathway strongly alleviates neutrophil recruitment and vaso-occlusion under inflammatory conditions in SCD. Finally, the results obtained by the inventors also suggest that plasmatic concentration of sTREM-1 could be a reliable biomarker for predicting vaso-occlusions and/or SCD-associated organ dysfunction and end-organ damage.

Methods of Treating:

The first object of the present invention relates to a method of treating (or reducing the severity of) a vaso-occlusion in a patient suffering from sickle cell disease comprising administering to the patient a therapeutically effective amount of a TREM-1 inhibitor.

As used herein, the term "sickle cell disease" or "SCD" has its general meaning in the art and refers to a hereditary blood disorder in which red blood cells assume an abnormal, rigid, sickle shape. Sickling of erythrocytes decreases the cells' flexibility and results in a risk of various life-threatening complications. The term includes sickle cell anemia, hemoglobin SC disease and Hemoglobin sickle beta-thalassemia. The term "sickle cell disease" encompasses any autosomal recessive genetic blood disorders characterized by the presence of at least one allele of the β-globin gene with the single mutation resulting in the hemoglobin variant hemoglobin S (also referred to as HbS).

As used herein, the term "patient" refers to a mammal, preferably a human. According to the present invention, a patient is a mammal, preferably a human, suffering from sickle cell disease and thus possessing hemoglobin variant(s), including at least one HbS, instead of hemoglobin HbA (major hemoglobin found in human adult subject).

In one embodiment, the SCD patient possesses either two alleles of the β-globin gene with the mutation resulting in HbS or one allele of the β-globin gene with the mutation resulting in HbS and another mutated allele of the β-globin gene. In one embodiment, said another mutated allele of the β-globin gene is an allele of the β-globin gene resulting in a variant other than HbS such as HbC, HbD, HbE or HbO or is an allele of the β-globin gene resulting in the partial or total loss of β-globin.

In one embodiment, the SCD patient possesses two alleles of the β-globin gene with the mutation resulting in HbS. Thus, in one embodiment, the sickle cell disease is hemoglobin SS disease (also referred to as sickle cell anemia).

As used herein, the term "vaso-occlusion" has its general meaning in the art and refers to a common complication of sickle cell disease which leads to the occlusion of capillaries and the restriction of blood flow to an organ, resulting in ischemia, with vascular dysfunction, tissue necrosis, and often organ damage. Vaso-occlusions are usually a constituent of vaso-occlusive crises, but they may also be more limited, clinically silent, and not cause hospitalization for vaso-occlusive crisis.

As used herein, the term "vaso-occlusive crisis" has its general meaning in the art and refers to a common painful complication of sickle cell disease which leads to hospitalization, in association with occlusion of capillaries and restrict blood flow to an organ resulting in ischemia, severe pain, necrosis, and most often with transient vaso-occlusions, and organ damage.

In particular, the TREM-1 inhibitor is thus particularly suitable for reperfusing the blood microcirculation of a patient suffering from VOC. Thus, the TREM-1 inhibitor is particularly suitable for reperfusing any tissue such as kidneys, liver, spleen, brain, bones, and/or lung of patients during VOC. More particularly, the TREM-1 is thus particularly suitable for the prevention of multi-organs failure. Even more particularly, the TREM-1 inhibitor is suitable for the treatment of acute chest syndrome. As used herein, the term "acute chest syndrome" or "ACS" refers to a frequent cause of acute lung disease in patients (in particular children) with sickle cell disease (SCD). Patients may present with ACS or may develop this complication during the course of a hospitalization for acute vaso-occlusive crises (VOC).

As used herein, the term "treatment" or "treat" refers to both prophylactic or preventive treatment as well as curative or disease modifying treatment, including treatment of patients at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular interval, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

In particular, the TREM-1 inhibitor is particularly suitable for the curative treatment of a vaso-occlusion in a patient suffering from sickle cell disease.

As used herein, the term "TREM-1" has its general meaning in the art and refers to the Triggering receptor expressed on myeloid cells 1. TREM-1 is a member of the Ig-superfamily, the expression of which is up-regulated on phagocytic cells in the presence of bacteria or fungi (Bouchon A et al. Nature 2001; 230:1103-7). An exemplary amino acid sequence is represented by SEQ ID NO: 1. It was previously described that TREM-1 can be shed or secreted from the membrane of activated phagocytes and can be found in a soluble form in body fluids. Accordingly, the term "sTREM-1" refers to the soluble form of the human TREM-1 receptor.

>sp|Q9NP99|TREM1_HUMAN Triggering
receptor expressed on myeloid cells 1 OS = Homo
sapiens OX = 9606 GN = TREM1 PE = 1 SV = 1
                                SEQ ID NO: 1
MRKTRLWGLLWMLFVSELRAATKLTEEKYELKEGQTLDVKCDYTLEKFAS

SQKAWQIIRDGEMPKTLACTERPSKNSHPVQVGRIILEDYHDHGLLRVRM

VNLQVEDSGLYQCVIYQPPKEPHMLFDRIRLVVTKGFSGTPGSNENSTQN

VYKIPPTTTKALCPLYTSPRTVTQAPPKSTADVSTPDSEINLTNVTDIIR

VPVFNIVILLAGGFLSKSLVFSVLFAVTLRSFVP

As used herein, the term "TREM-1 inhibitor" refers to any compound, chemical, antibody, or peptide, naturally occurring or synthetic, that directly or indirectly decreases the activity and/or expression of TREM-1. Functionally conservative variations of known TREM-1 inhibitors are also intended to be covered by this description. This includes, for example only, deuterated variations of known inhibitors, inhibitors comprising non-naturally occurring amino-acids, functional variations of peptide inhibitors involving a different sequence of amino acids, inhibitors created by codon variations which code for the same amino-acid sequence of a known inhibitor or functional variation thereof, versions of peptides described herein in which one or more of the amino acids can be, individually, D or L isomers. The invention also includes combinations of L-isoforms with D-isoforms.

Common TREM-1 inhibitors include peptides which may be derived from TREM-1, or TREM-like-transcript-1 ("TLT-1"). Any peptide which competitively binds TREM-1 ligands, thereby reducing TREM-1 activity and/or expression is a TREM-1 inhibitor. These peptides may be referred to as "decoy receptors."

In some embodiments, the TREM-1 inhibitor is a peptide that is disclosed in WO2014037565. Examples of such peptides are listed below in Table A. LR17 is a known, naturally occurring direct inhibitor of TREM-1 which functions by binding and trapping TREM-1 ligand. LR12 is a 12 amino-acid peptide derived from LR17. LR12 is composed of the N-terminal 12 amino-acids from LR17. Research suggests that LR12 is an equivalent TREM-1 inhibitor when compared to LR17. LR6-1, LR6-2 and LR6-3 are all 6 amino-acids peptides derived from LR17. These peptides may function in the same manner as LR12.

TABLE A

| Different peptides that can be used as TREM-1 inhibitors | | |
|---|---|---|
| Peptide name | Sequence | SEQID |
| LR17 | LQEEDAGEYGCMVDGAR | SEQ ID NO: 2 |
| LR12 | LQEEDAGEYGCM | SEQ ID NO: 3 |
| LR6-1 | LQEEDA | SEQ ID NO: 4 |
| LR6-2 | EDAGEY | SEQ ID NO: 5 |
| LR6-3 | GEYGCM | SEQ ID NO: 6 |
| LP17 | LQVEDSGLYQCVIQHPP | SEQ ID NO: 7 |

TABLE A-continued

Different peptides that can be used as
TREM-1 inhibitors

| Peptide name | Sequence | SEQID |
|---|---|---|
| LP12 | LQVEDSGLYQCV | SEQ ID NO: 8 |
| LP6-1 | LQVEDS | SEQ ID NO: 9 |
| LP6-2 | EDSGLY | SEQ ID NO: 10 |
| LP6-3 | GLYQCV | SEQ ID NO: 11 |

Additional examples of TREM-1 inhibitors include those disclosed by patent application WO 2015018936. These include, but are not limited to, antibodies directed to TREM-1 and/or sTREM-1 or TREM-1 and/or sTREM-1 ligand, small molecules inhibiting the function, activity or expression of TREM-1, peptides inhibiting the function, activity or expression of TREM-1, siRNAs directed to TREM-1, shRNAs directed to TREM-1, antisense oligo-nucleotide directed to TREM-1, ribozymes directed to TREM-1 and aptamers which bind to and inhibit TREM-1. Antibodies have been shown to inhibit TREM-1 as well. Representative antibodies are described, for example, in U.S. Publication No. 20130309239 and U.S. Pat. No. 9,000, 127. Additional examples of TREM-1 inhibitors also include those disclosed in WO2011 047097. As described in U.S. patent publications 20090081199 and 20030165875, fusion proteins between human IgG1 constant region and the extracellular domain of mouse TREM-1 or that of human TREM-1 can be used, as a decoy receptor, to inhibit TREM-1. Another TREM-1 inhibitor is TLT-1, as disclosed in Washington, et al., "A TREM family member, TLT-1, is found exclusively in the alpha-granules of megakaryocytes and platelets," Blood. 2004 Aug. 15; 104(4):1042-7. Additional TREM-1 inhibitors include MicroRNA 294, which has been shown to target TREM-1 by dual-luciferase assay activity. Naturally-occurring TREM-1 inhibitors include curcumin and diferuloylmethane, a yellow pigment present in turmeric. Inhibition of TREM-1 by curcumin is oxidant independent. Accordingly, curcumin and synthetic curcumin analogs, such as those disclosed in U.S. Publication Nos. 20150087937, 20150072984, 20150011494, 20130190256; 20130156705, 20130296527, 20130224229, 20110229555; and 20030153512; U.S. Pat. Nos. 7,947,687, 8,609,723, and PCT WO 2003105751.

In one embodiment, the TREM-1 inhibitor is a peptide derived from TLT-1 or TREM-1, in particular peptides as described herein.

In one embodiment, the TREM-1 inhibitor is a short TLT-1 peptide consisting of less than 50 amino acids, preferably consisting of between 6 and 20 amino acids, more preferably consisting of between 6 and 17 amino acids, wherein said TLT-1 peptide comprises between 6 and 20 consecutive amino acids from the human TLT-1 having an amino acid sequence as set forth in SEQ ID NO: 12 (MGLTLLLLLLLLGLEGQGIVGSLPEVLQAPVGSSIL-VQCHYRLQDVKAQKVWCRFLPE GCQPLVSSAVDR-RAPAGRRTFLTDLGGGLLQVEMVTLQEED-AGEYGCMVDGARGP QILHRVSLNILPPEEEEE-THKIGSLAENAF SDPAGSANPLEPSQDEKSIPLIW-GAVLLVG LLVAAVVLFAVMAKRKQGNRLGV-CGRFLSSRVSGMNPSSVVHHVSDSGPAAELPLD VPHIRLDSPPSFDNTTYTSLPLDSPSGKPSLPAPSSLP-PLPPKVLVCSKPVTYATVIFPGG NKGGGTSCGPA- QNPPNNQTPSS); or a sequence having at least 60, 65, 70, 75, 80, 85 or 90% identity with the amino acid sequence as set forth in SEQ ID NO: 12; or a function-conservative variant or derivative thereof.

In one embodiment, the TREM-1 inhibitor is a TLT-1 peptide consisting of 6 to 12, 13, 14, 15, 16, 17, 18, 19 or 20 amino acids and comprising an amino acid sequence as set forth in SEQ ID NO: 2, SEQ ID NO: 3, SEQ ID NO: 4, SEQ ID NO: 5 or SEQ ID NO: 6, or a sequence having at least 60, 65, 70, 75, 80, 85 or 90% identity with the amino acid sequence as set forth in SEQ ID NO: 2, SEQ ID NO: 3, SEQ ID NO: 4, SEQ ID NO: 5, or SEQ ID NO: 6, respectively; or a function-conservative variant or derivative thereof.

In one embodiment, the TREM-1 inhibitor is a TLT-1 peptide comprising or consisting of an amino acid sequence as set forth in SEQ ID NO: 2, SEQ ID NO: 3, SEQ ID NO: 4, SEQ ID NO: 5, or SEQ ID NO: 6; or a sequence having at least 60, 65, 70, 75, 80, 85 or 90% identity with the amino acid sequence as set forth in SEQ ID NO: 2, SEQ ID NO: 3, SEQ ID NO: 4, SEQ ID NO: 5, or SEQ ID NO: 6, respectively; or a function-conservative variant or derivative thereof.

In one embodiment, the TREM-1 inhibitor is a TLT-1 peptide having an amino acid sequence as set forth in SEQ ID NO: 2, SEQ ID NO: 3, SEQ ID NO: 4, SEQ ID NO: 5, or SEQ ID NO: 6; or a sequence having at least 60, 65, 70, 75, 80, 85 or 90% identity with the amino acid sequence as set forth in SEQ ID NO: 2, SEQ ID NO: 3, SEQ ID NO: 4, SEQ ID NO: 5, or SEQ ID NO: 6, respectively; or a function-conservative variant or derivative thereof.

In one embodiment, the TREM-1 inhibitor is a TLT-1 peptide having an amino acid sequence as set forth in SEQ ID NO: 3, also known as LR12; or a sequence having at least 60, 65, 70, 75, 80, 85 or 90% identity with the amino acid sequence as set forth in SEQ ID NO: 3; or; or a function-conservative variant or derivative of SEQ ID NO: 3.

In one embodiment, the TREM-1 inhibitor is a short TREM-1 peptide consisting of less than 50 amino acids, preferably consisting of between 6 and 20 amino acids, more preferably consisting of between 6 and 17 amino acids, wherein said TREM-1 peptide comprises between 6 and 20 consecutive amino acids from the human TREM-1 having an amino acid sequence as set forth in SEQ ID NO: 1 or a function-conservative variant or derivative thereof.

In one embodiment, the TREM-1 inhibitor is a TREM-1 peptide consisting of 6 to 12, 13, 14, 15, 16, 17, 18, 19 or 20 amino acids and comprising an amino acid sequence as set forth in SEQ ID NO: 7, SEQ ID NO: 8, SEQ ID NO: 9, SEQ ID NO: 10 or SEQ ID NO: 11; or a sequence having at least 60, 65, 70, 75, 80, 85 or 90% identity with the amino acid sequence as set forth in SEQ ID NO: 7, SEQ ID NO: 8, SEQ ID NO: 9, SEQ ID NO: 10 or SEQ ID NO: 11, respectively; or a function-conservative variant or derivative thereof.

In one embodiment, the TREM-1 inhibitor is a TREM-1 peptide comprising or consisting of an amino acid sequence as set forth in SEQ ID NO: 7, SEQ ID NO: 8, SEQ ID NO: 9, SEQ ID NO: 10 or SEQ ID NO: 11; or a sequence having at least 60, 65, 70, 75, 80, 85 or 90% identity with the amino acid sequence as set forth in SEQ ID NO: 7, SEQ ID NO: 8, SEQ ID NO: 9, SEQ ID NO: 10 or SEQ ID NO: 11, respectively; or a function-conservative variant or derivative thereof.

In one embodiment, the TREM-1 inhibitor is a TREM-1 peptide having an amino acid sequence as set forth in SEQ ID NO: 7, SEQ ID NO: 8, SEQ ID NO: 9, SEQ ID NO: 10 or SEQ ID NO: 11 or a sequence having at least 60, 65, 70, 75, 80, 85 or 90% identity with the amino acid sequence as set forth in SEQ ID NO: 7, SEQ ID NO: 8, SEQ ID NO: 9, SEQ ID NO: 10 or SEQ ID NO: 11, respectively; or a function-conservative variant or derivative thereof.

In the present invention, the term "identity" or "identical", when used in a relationship between the sequences of two or more peptides, refers to the degree of sequence relatedness between peptides, as determined by the number of matches between strings of two or more amino acid residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

As used herein, the term "function-conservative variants" denotes peptides derived from the peptides as described herein, in which a given amino acid residue in a peptide has been changed without altering the overall conformation and function of said peptides, including, but not limited to, replacement of an amino acid with one having similar properties (such as, for example, similar polarity, similar hydrogen bonding potential, acidic or basic amino acid replaced by another acidic or basic amino acid, hydrophobic amino acid replaced by another hydrophobic amino acid, aromatic amino acid replaced by another aromatic amino acid).

It is commonly known that amino acids other than those indicated as conserved may differ in a peptide so that the percent of amino acid sequence similarity between any two peptides of similar function may vary and may be, for example, from 70% to 99% as determined according to an alignment method such as by the Cluster Method, wherein similarity is based on the MEGALIGN algorithm.

A "function-conservative variant" also includes peptides which have at least 20%, 30%, 40%, 50%, or 60% amino acid identity with the peptides as described herein, for example as determined by BLAST or FASTA algorithms, and which have the same or substantially similar properties or functions as the peptides as described herein. Preferably "function-conservative variants" include peptides which have at least 60%, 65%, 70%, 75%, 80%, 85% or 90% amino acid identity with the peptides as described herein and which have the same or substantially similar properties or functions as the peptides as described hereinabove.

As used herein, the term "derivative" refers to a variation of a peptide or of a function-conservative variant thereof that is otherwise modified in order to alter the in vitro or in vivo conformation, activity, specificity, efficacy or stability of the peptide. For example, said variation may encompass modification by covalent attachment of any type of molecule to the peptide or by addition of chemical compound(s) to any of the amino-acids of the peptide.

In one embodiment, the peptide or function-conservative variants or derivatives thereof as described hereinabove may have D- or L-configuration.

In one embodiment, the amino acid from the amino end of the peptide or function-conservative variant or derivative thereof as described hereinabove has an acetylated terminal amino group, and the amino acid from the carboxyl end has an amidated terminal carboxy group.

In addition, the peptide or function-conservative variant or derivative thereof as described hereinabove may undergo reversible chemical modifications in order to increase its bioavailability (including stability and fat solubility) and its ability to pass the blood-brain barrier and epithelial tissue. Examples of such reversible chemical modifications include esterification of the carboxy groups of glutamic and aspartic amino acids with an alcohol, thereby removing the negative charge of the amino acid and increasing its hydrophobicity. This esterification is reversible, as the ester link formed is recognized by intracellular esterases which hydrolyze it, restoring the charge to the aspartic and glutamic residues. The net effect is an accumulation of intracellular peptide, as the internalized, de-esterified peptide cannot cross the cell membrane.

Another example of such reversible chemical modifications includes the addition of a further peptide sequence, which allows the increase of the membrane permeability, such as a TAT peptide or Penetratin peptide (see—Charge-Dependent Translocation of the Trojan. A Molecular View on the Interaction of the Trojan Peptide Penetratin with the 15 Polar Interface of Lipid Bilayers. Biophysical Journal, Volume 87, Issue 1, 1 Jul. 2004, Pages 332-343).

The peptides or function-conservative variants or derivatives thereof as described hereinabove may be obtained through conventional methods of solid-phase chemical peptide synthesis, following Fmoc and/or Boc-based methodology (see Pennington, M. W. and Dunn, B. N. (1994). Peptide synthesis protocols. Humana Press, Totowa.).

Alternatively, the peptides or function-conservative variants or derivatives as described hereinabove may be obtained through conventional methods based on recombinant DNA technology, e.g., through a method that, in brief, includes inserting the nucleic acid sequence coding for the peptide into an appropriate plasmid or vector, transforming competent cells for said plasmid or vector, and growing said cells under conditions that allow the expression of the peptide and, if desired, isolating and (optionally) purifying the peptide through conventional means known to experts in these matters or eukaryotic cells that express the peptide. A review of the principles of recombinant DNA technology may be found, for example, in the text book entitled "Principles of Gene Manipulation: An Introduction to Genetic Engineering," R. W. Old & S. B. Primrose, published by Blackwell Scientific Publications, 4th Edition (1989).

By a "therapeutically effective amount" of the agent is meant a sufficient amount of the TREM-1 inhibitor to treat vaso-occlusion in the subject. It will be understood, however, that the total daily usage of the agent is decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific agent; and like factors well known in the medical arts. For example, it is well within the skill of the art to start doses of the compound at levels lower than those required to achieve the desired therapeutic effect and to gradually increase the dosage until the desired effect is achieved. However, the daily dosage of the agent may be varied over a wide range from 0.01 to 1,000 mg per adult per day. Preferably, the compositions contain 0.01, 0.05, 0.1, 0.5, 1.0, 2.5, 5.0, 10.0, 15.0, 25.0, 50.0, 100, 250 and 500 mg of the agent for the symptomatic adjustment of the dosage to the subject to be treated. A medicament typically contains from about 0.01 mg to about 500 mg of the active ingredient, preferably from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Typically, the inhibitor of the present invention is combined with pharmaceutically acceptable excipients, and optionally sustained-release matrices, such as biodegradable polymers, to form pharmaceutical compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Sterile injectable solutions are prepared by incorporating the active ingredient at the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Methods of Predicting:

A further object of the present invention relates to a method of determining whether a patient suffering from sickle cell disease has or is at risk of having vaso-occlusion comprising determining the level of sTREM-1 in a biological sample, preferably in a blood sample, obtained from the patient wherein said level indicates whether or not the patient has or is at risk of having vaso-occlusion.

As used herein, the term "risk" relates to the probability that an event will occur over a specific time period, as in the conversion to vaso-occlusion, and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula $p/(1-p)$ where p is the probability of event and $(1-p)$ is the probability of no event) to no-conversion. Alternative continuous measures, which may be assessed in the context of the present invention, include time to vaso-occlusion conversion and therapeutic vaso-occlusion conversion risk reduction ratios. "Risk evaluation," or "evaluation of risk" in the context of the present invention encompasses making a prediction of the probability, odds, or likelihood that an event or disease state may occur, the rate of occurrence of the event or conversion from one disease state to another, i.e., from a normal condition to vaso-occlusion or to one at risk of developing vaso-occlusion. Risk evaluation can also comprise prediction of future clinical parameters, traditional laboratory risk factor values, or other indices of vaso-occlusion, such as alcohol consumption or cigarette smoking, either in absolute or relative terms in reference to a previously measured population. The methods of the present invention may be used to make continuous or categorical measurements of the risk of conversion to vaso-occlusion, thus diagnosing and defining the risk spectrum of a category of subjects defined as being at risk for vaso-occlusion. In the categorical scenario, the invention can be used to discriminate between normal and other subject cohorts at higher risk for vaso-occlusion. In some embodiments, the present invention may be used so as to discriminate those at risk for developing vaso-occlusion from those having vaso-occlusion, or those having vaso-occlusion from normal.

In some embodiment, the patient suffering from sickle cell disease has or is at risk of having chronic vascular and tissue injury.

In some embodiment, the present invention relates to a method of determining whether a patient suffering from sickle cell disease has or is at risk of having chronic vascular and tissue injury comprising determining the level of sTREM-1 in a blood sample obtained from the patient wherein said level indicates whether or not the patient has or is at risk of having chronic vascular and tissue injury.

As used herein, the term "chronic vascular and tissue injury" refers to a chronic injury to a blood vessel, a tissue, an artery or a vein.

In some embodiment, the chronic vascular and tissue injury include but are not limited to sickle cell nephropathy, progressive cerebrovascular remodeling, cognitive impairment, osteonecrosis, leg ulcers, retinopathy, pulmonary arterial hypertension.

As used herein the term "blood sample" means a whole blood, serum, or plasma sample obtained from the patient. Preferably the blood sample according to the invention is a plasma sample.

In one embodiment, the term "level" as used herein refers to the expression level of sTREM-1. It can refer alternatively to the translation level of sTREM-1 or to the transcription level of sTREM-1. In one embodiment, the level of sTREM-1 refers to the translation level of sTREM-1.

According to one embodiment, the term "level" as used herein refers to the quantity, amount or concentration of sTREM-1. Thus, the level of sTREM 1 measured in a biological sample (preferably in a blood sample) from a human subject refers to the quantity, amount or concentration of sTREM-1 in said biological sample.

According to one embodiment, the level of sTREM-1 refers to a protein level, a protein quantity, a protein amount or a protein concentration.

The measurement of the level of sTREM-1 in the blood sample is typically carried out using standard protocols known in the art. For example, the method may comprise contacting the blood sample with a binding partner capable of selectively interacting with sTREM-1 in the sample. In some embodiments, the binding partners are antibodies, such as, for example, monoclonal antibodies or even aptamers. For example the binding may be detected through use of a competitive immunoassay, a non-competitive assay system using techniques such as western blots, a radioimmunoassay, an ELISA (enzyme linked immunosorbent assay), a "sandwich" immunoassay, an immunoprecipitation assay, a precipitin reaction, a gel diffusion precipitin reaction, an immunodiffusion assay, an agglutination assay, a complement fixation assay, an immunoradiometric assay, a fluorescent immunoassay, a protein A immunoassay, an immunoprecipitation assay, an immunohistochemical assay, a competition or sandwich ELISA, a radioimmunoassay, a Western blot assay, an immunohistological assay, an immunocytochemical assay, a dot blot assay, a fluorescence polarization assay, a scintillation proximity assay, a homogeneous time resolved fluorescence assay, a IAsys analysis, and a BIAcore analysis. The aforementioned assays generally involve the binding of the partner (ie. antibody or aptamer) to a solid support. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like. An exemplary biochemical test for identifying specific proteins employs a standardized test format, such as ELISA test, although the information provided herein may apply to the development of other biochemical or diagnostic tests and is not limited to the development of an ELISA test (see, e.g., Molecular Immunology: A Textbook, edited by Atassi et al. Marcel Dekker Inc., New York and Basel 1984, for a description of ELISA tests). Therefore, ELISA method can be used, wherein the wells of a microtiter plate are coated with a set of antibodies which recognize sTREM-1. A sample containing or suspected of containing sTREM-1 is then added to the coated wells. After a period of incubation sufficient to allow the formation of antibody-antigen complexes, the plate(s)

can be washed to remove unbound moieties and a detectably labelled secondary binding molecule added. The secondary binding molecule is allowed to react with any captured sample marker protein, the plate washed and the presence of the secondary binding molecule detected using methods well known in the art. Measuring the level of sTREM-1 (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, said one or two biomarkers proteins may be identified based on the known "separation profile" e.g., retention time, for that compound and measured using standard techniques. Alternatively, the separated compounds may be detected and measured by, for example, a mass spectrometer. Typically, levels of immunoreactive sTREM-1 in a sample may be measured by an immunometric assay on the basis of a double-antibody "sandwich" technique, with a monoclonal antibody specific for sTREM-1 (Cayman Chemical Company, Ann Arbor, Michigan). According to said embodiment, said means for measuring sTREM-1 level are for example i) a sTREM-1 buffer, ii) a monoclonal antibody that interacts specifically with sTREM-1, iii) an enzyme-conjugated antibody specific for sTREM-1 and a predetermined reference value of sTREM-1.

In some embodiments, the method further comprises the steps of ii) comparing the level of sTREM-1 determined in the blood sample obtained from the patient with a predetermined reference value wherein a differential between the determine level of sTREM-1 and the predetermined reference value indicates whether or not the patient has or is at risk of having vaso-occlusion.

Typically, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of sTREM-1 level in properly banked historical patient samples may be used in establishing the predetermined reference value. The threshold value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after calculating the level of sTREM-1 in a group of reference, one can use algorithmic analysis for the statistic treatment of the determined levels in samples to be tested, and thus obtain a classification standard having significance for sample classification. The full name of ROC curve is Receiver Operator Characteristic Curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGN-ROC.FOR, MULTIREADER POWER.SAS, CREATEROC.SAS, GB STAT VI0.0 (Dynamic Microsystems, Inc. Silver Spring, Md., USA), etc.

The method of the present invention is thus particularly suitable for stratifying the risk in the patients and make the choice of the most appropriate therapeutic strategy. In particular, when it is concludes that the patient has or is at risk of having vaso-occlusion, then it can be decided to treat the patient with a therapeutically amount of an agent suitable for reperfusing the capillaries and the microcirculation (e.g. a TREM-1 inhibitor as described above, or hydroxyurea).

The invention will be further illustrated by the following figures and examples. However, these examples and figures should not be interpreted in any way as limiting the scope of the present invention.

EXAMPLE

Figure 1A:
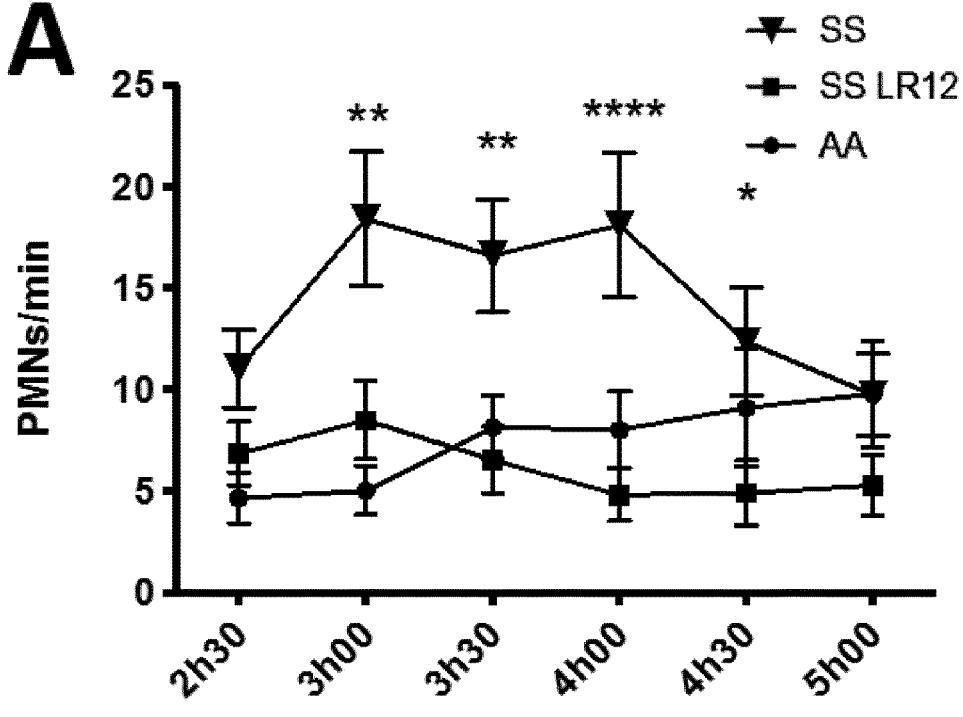
FIG. 1: Results of intravital microscopy obtained by observation of neutrophils in the post-capillary venous microcirculation of the cremaster of HbSS knock-in sickle cell mice, after injection of TNFα. (A-C) The LR12 allows a significant reduction in neutrophil rolling between 3 h and 4 h30 post-injection of TNFα (A, 2way ANOVA P value=0.0041), their adhesion throughout the experiment (B, 2way ANOVA P value <0.0001), and their transmigration from 3 h to 5 h post-TNFα (C, 2way ANOVA P value <0.0001). (D-I) Post-microscopy blood count. * p<0.05,  p<0.01, * p<0.001, **** p<0.0001. SS (n=5), SS LR12 (n=6), AA (n=5).

Methods:

Mouse Model and Study Design

Experiments were performed on 4-6 week-old sex matched healthy control (Hba$^{tm1(HBA)Tow}$ Hbb$^{tm3(HBG1,HBB)~Tow}$) (HbAA (hα/hα::β$^A$/β$^A$)) and SCD (Hba$^{tm1(HBA)Tow}$ Hbb$^{tm2(HBG1,HBB*)Tow}$) (HbSS (hα/hα::βS/βS)) mice as well as SAD transgenic sickle mice with or without Trem-1 gene deletion (TREM-1 KO). The animal protocol was approved by the Paris Descartes University Animal Care and Use Committee and the French Ministry of Agriculture. Animals were anesthetized with isoflurane, and whole blood was collected from each mouse via retro-orbital venipuncture by heparinized microcapillaries. In anesthetized animals, organs were immediately removed and divided into two and either immediately frozen in liquid nitrogen or fixed in 10% formalin and embedded in paraffin for histology.

In order to test the pharmacological inhibition of TREM-1 on erythrocyte vascular congestion and neutrophils infiltrates, homozygous HbS (SS) mice were subjected to 14 hours hypoxia (8% oxygen) and then 1 hours reoxygenation (21% oxygen) to trigger acute vaso-occlusive crisis as previously described (Sabaa N et al. J Clin Invest. 2008 May; 118(5):1924-33). The TREM-1 inhibitory peptide for each of the hypoxia-reoxygenation experiments was administered by intraperitoneal injection just prior to the onset of hypoxia, as well as at the end of hypoxia, at the beginning of the reoxygenation phase. These conditions reproduce a situation of severe hypoxia for SCD, provoking crises and damage related to ischemia-reperfusion. After this experiment, the tissues were analyzed in the same way as for the SS mice in the base state.

Intravital Video Microscopy Experimental Protocol:

To characterize in vivo the effects of the TREM-1 pathway on neutrophils recruitment, we used a protocol as previously described (Koehl B et al. Haematologica. 2017 July; 102(7):1161-1172). Male mice were anaesthetized by spontaneous inhalation of isoflurane and maintained at 37° C. with a heating pad. The left jugular vein was cannulated to administer drugs and antibodies. The left cremaster muscle was exposed and mounted for intravital microscopic observations of the cremasteric microcirculation and adjacent tissue. The muscle was superfused with 36° C. warmed bicarbonate-buffered saline pH 7.4. LR12 peptide, or equivalent volume of vehicle (isotonic saline) were injected 10 min before (6 mg/kg) and 3 h15 after (3 mg/kg) intrascrotal injection of 0.5 μg tumor necrosis factor (TNFα, R&D Systems). 2 h after TNFα injection, the cremaster muscle was incised and neutrophils were monitored by injection of labeled Phycoerythrin-conjugated anti-Ly6G antibody (0.05 μg/g body weight, clone RB6-8C5, BD Biosciences Pharmingen). Venules were visualized with an intravital microscope (Zeiss Examiner D1) equipped with a water-immersion objective (Zeiss Plan-Apochromat 20×/1.0 NA) and fluorescence excitation was made through a Lambda DG-4 high-speed wavelength switcher (Sutter Instrument). Images were collected with a 512×512 pixel back-thinned EMCCD camera (Evolve, Photometrics). Images were analyzed using SlideBook 6.0 software (Intelligent Imaging Innovations). The neutrophil rolling flux fraction, adhesion density, adhesion efficiency and transmigration were measured using playback assessment of 3-min digital time-lapse videos and 3D z-stack recordings of single unbranched venules (3 venules per mouse, 20-40 μm) from 2.5 hours to 5 hours after the TNFα challenge at 30-min intervals. Vessel diameter and wall shear rate measure methods are described in (Koehl B et al. Haematologica. 2017 July; 102(7):1161-1172). Blood samples used to determine blood counts were taken immediately after recording (Hemavet, Drew scientific).

Assessment of TREM-1 Plasma Concentrations:

The animals' blood was collected in EDTA anticoagulated tubes (Minicollect, BD). After centrifugation (5000 g, 10 min, 4° C.), plasma samples were aliquoted and stored at −80° C. An ELISA kit was used to perform the TREM-1 plasma assay (DuoSet Mouse TREM-1, R & D Systems, #DY1187) and the results are extracted from the reading of the optical density by a spectrophotometer as recommended by the manufacturer.

Figure 1B:
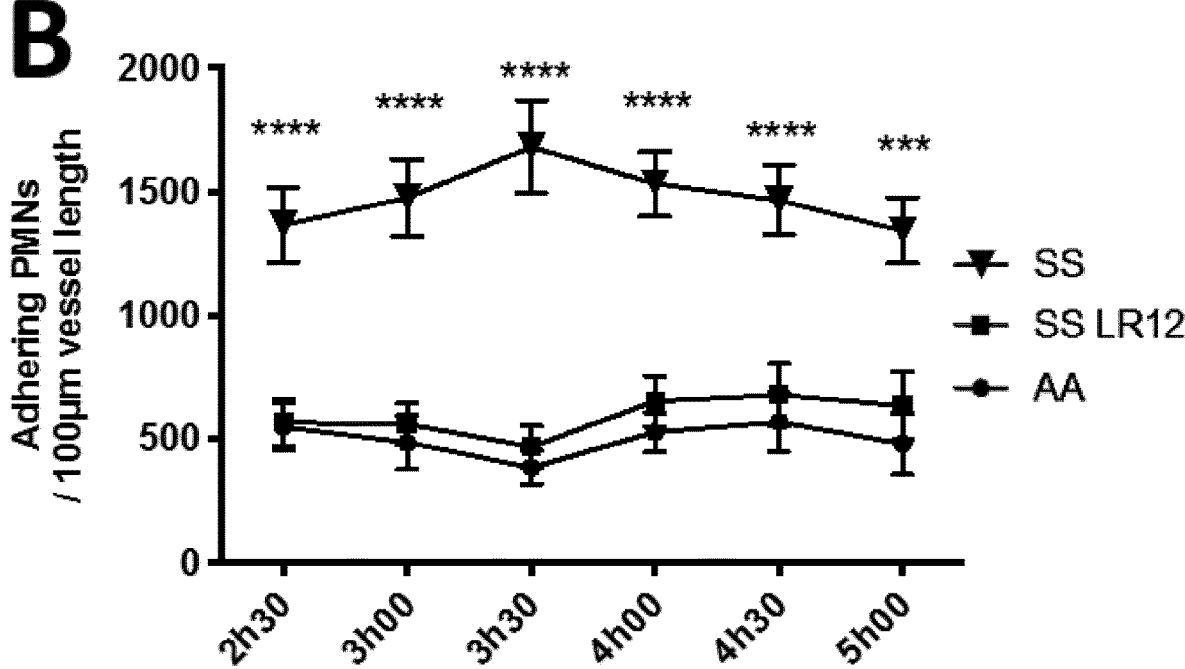
Figure 1C:
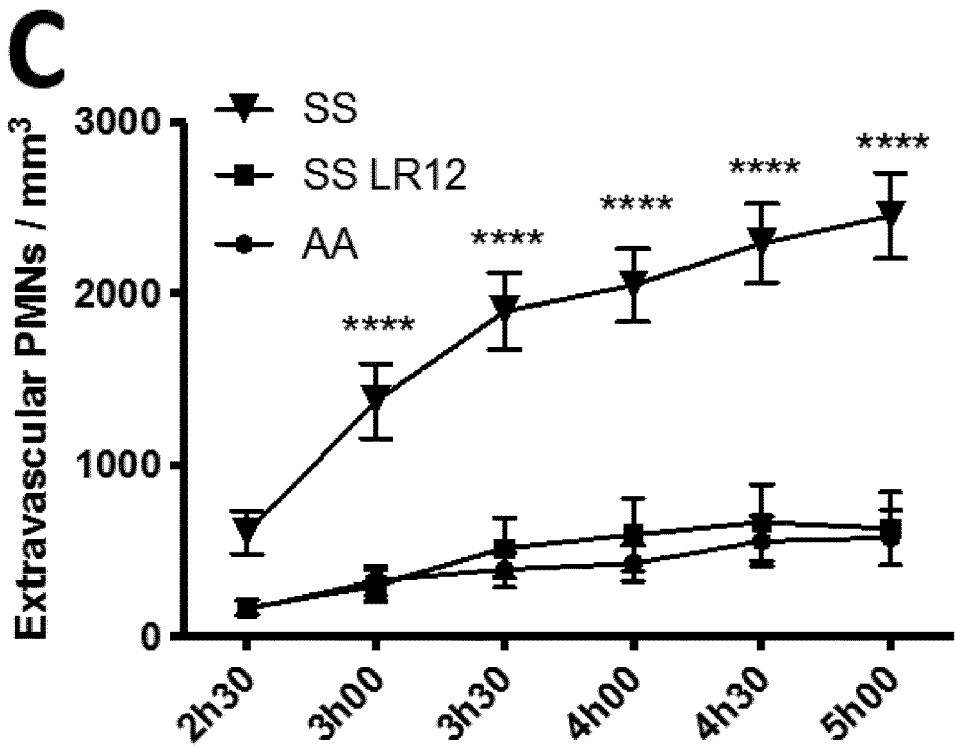
Figure 2A:
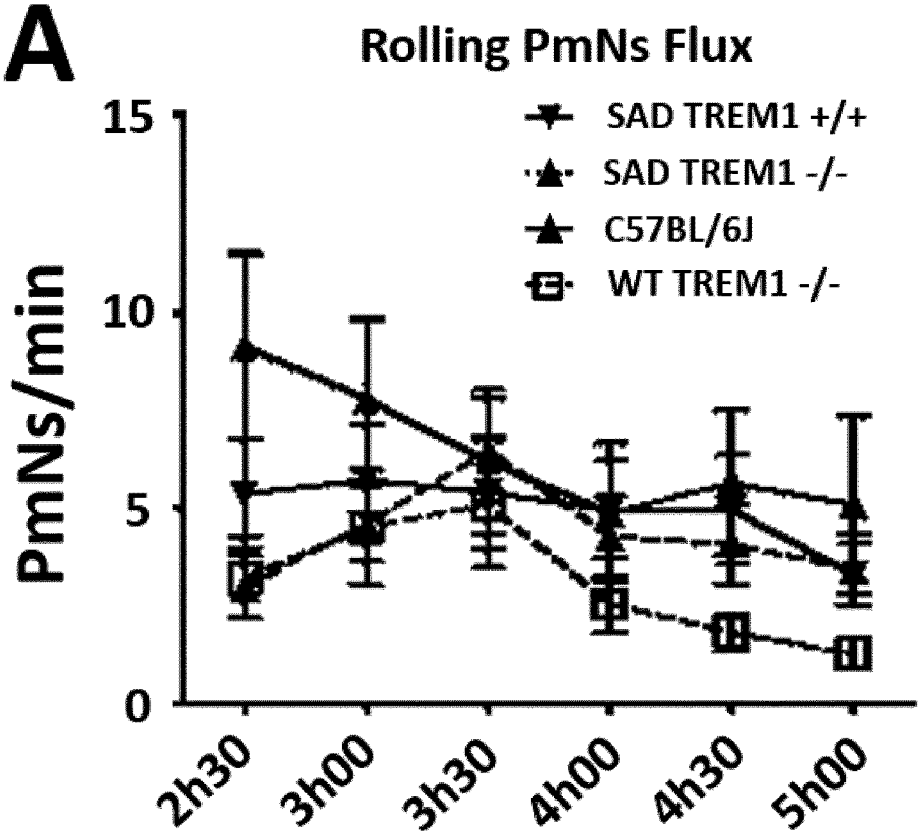
FIG. 2: Results of intravital microscopy obtained by observation of neutrophils in the post-capillary venous microcirculation of cremaster of Trem-1 gene knock-out (TREM-1 KO) sickle cell mice (SAD background), after injection of TNFα at TO. (A-C) The genetic deletion of Trem-1 gene allows a significant reduction in neutrophil adhesion throughout the experiment (B, 2way ANOVA P value <0.0001), and their transmigration (C, 2way ANOVA P value <0.0021). *=SAD TREM-1+/+vs SAD TREM-1-/-. * P<0.05,  p<0.01, ** p<0.0001. SAD TREM-1+/+ (n=5), SAD TREM-1-/-(n=5), wild-type (WT) (C57BL/6J) TREM-1+/+(n=4), WT TREM-1-/-(n=4)).
Figures 2B, 2C:
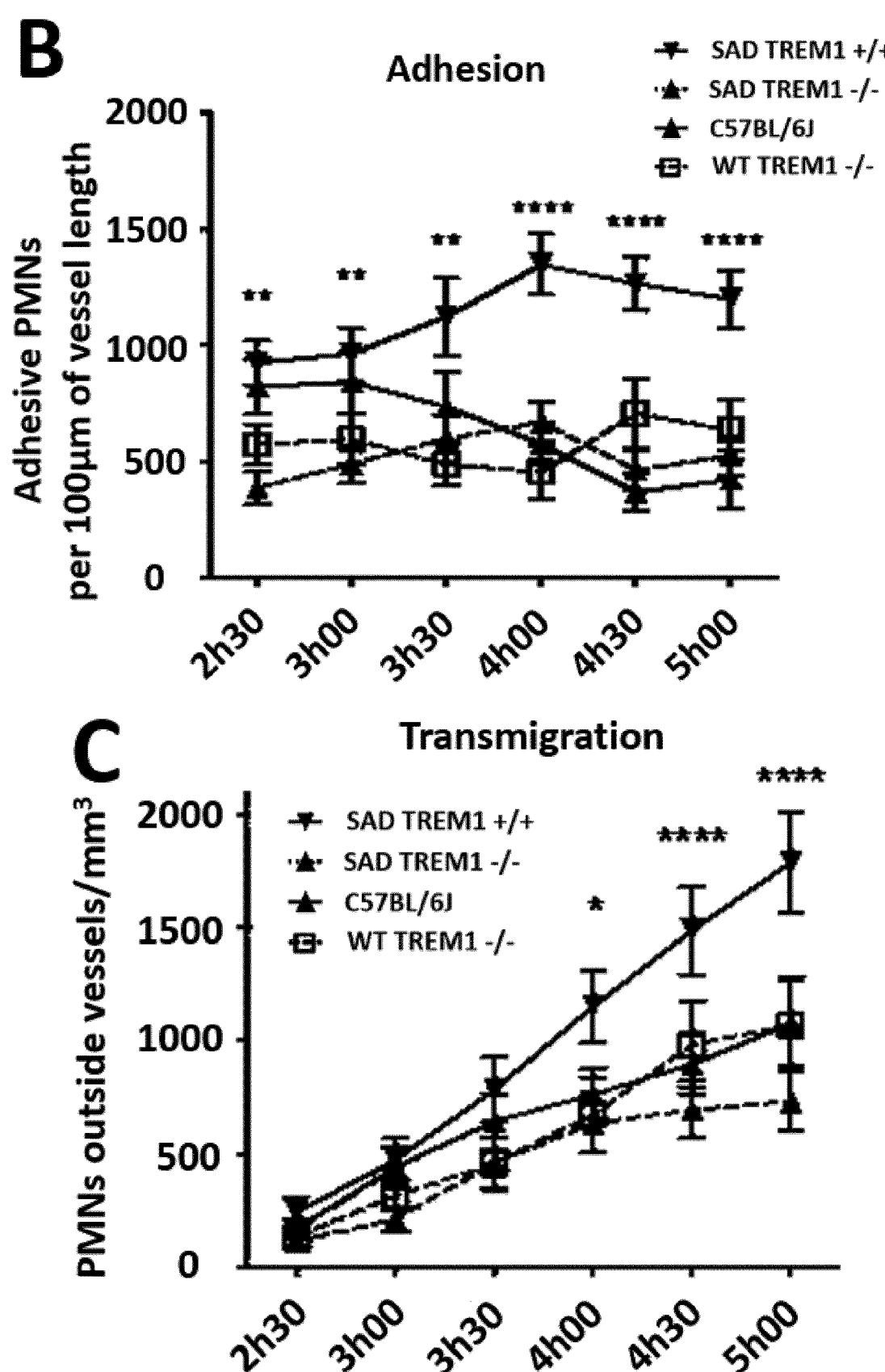
Figure 3A:
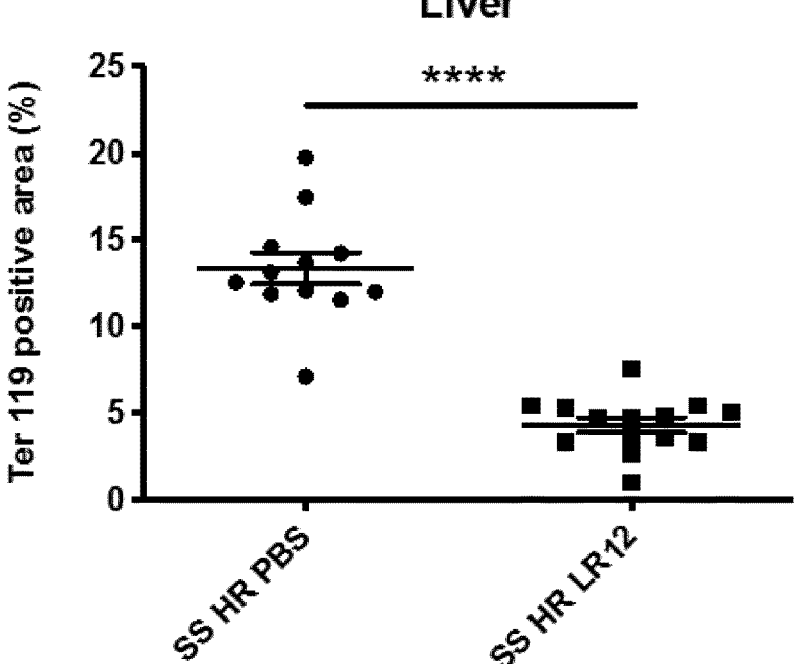
FIG. 3: LR12 administration promoted a significant reduction vascular congestion with Ter 119+ erythrocytes in sickle cell mice as observed in histological sections of liver (A), spleen (B) and renal medulla (D), but not in lung sections (C). * p<0.05, **** p<0.0001. Scale=50 μm. SS PBS (n=12), SS LR12 (n=14).
Figure 3B:
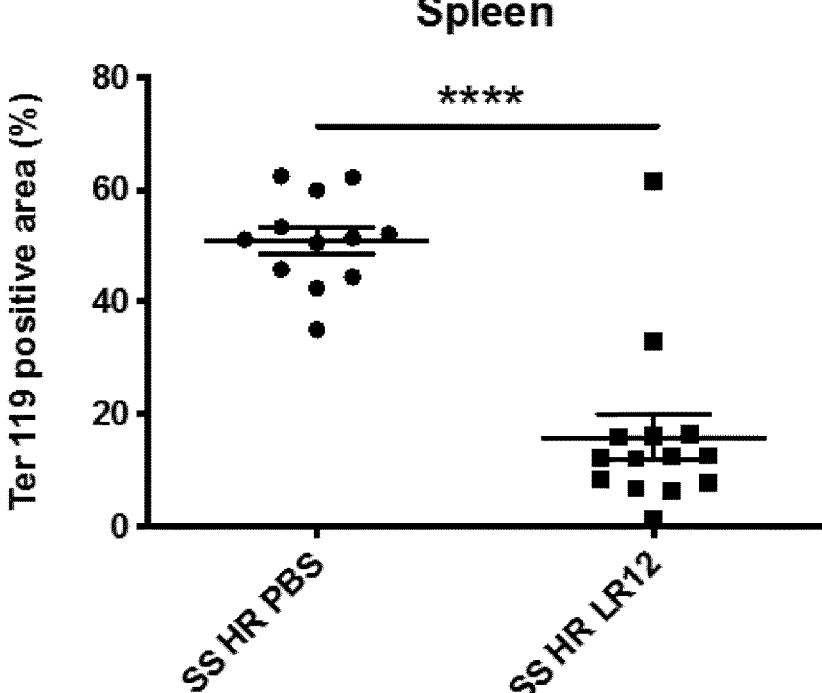
Figure 3C:
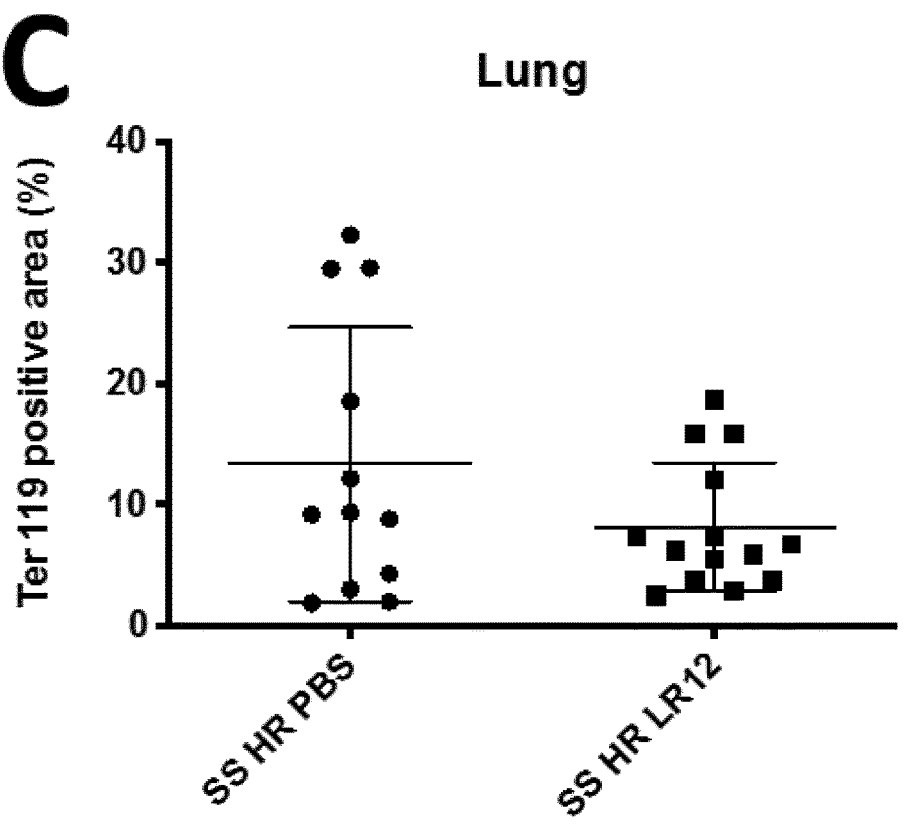
Figure 3D:
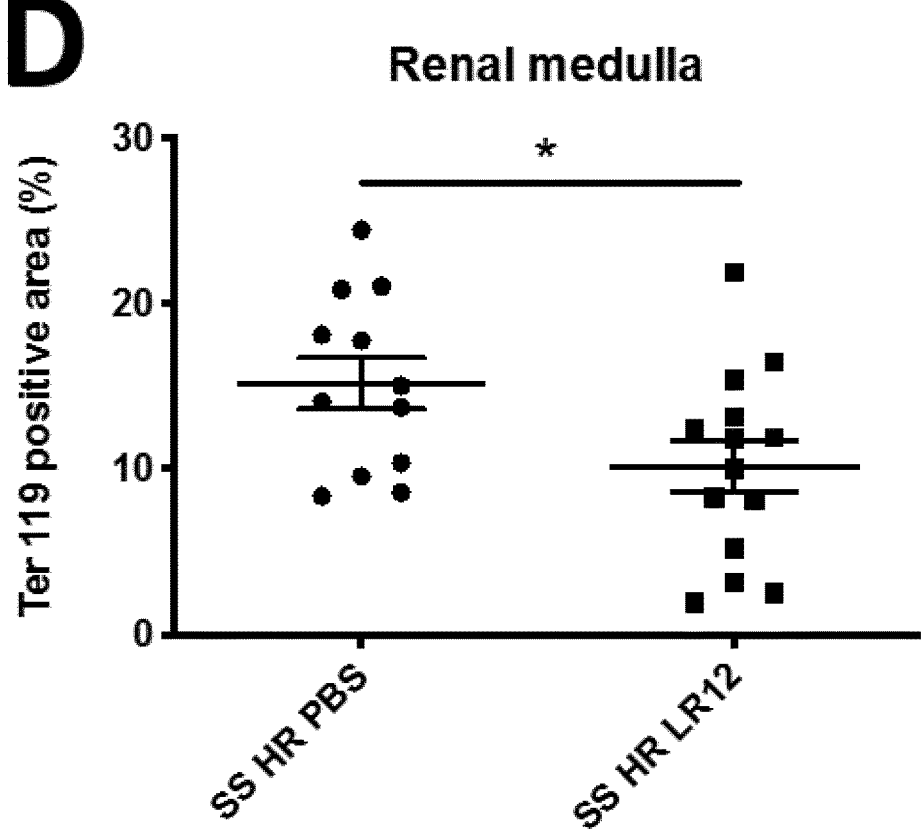
Figure 4A:
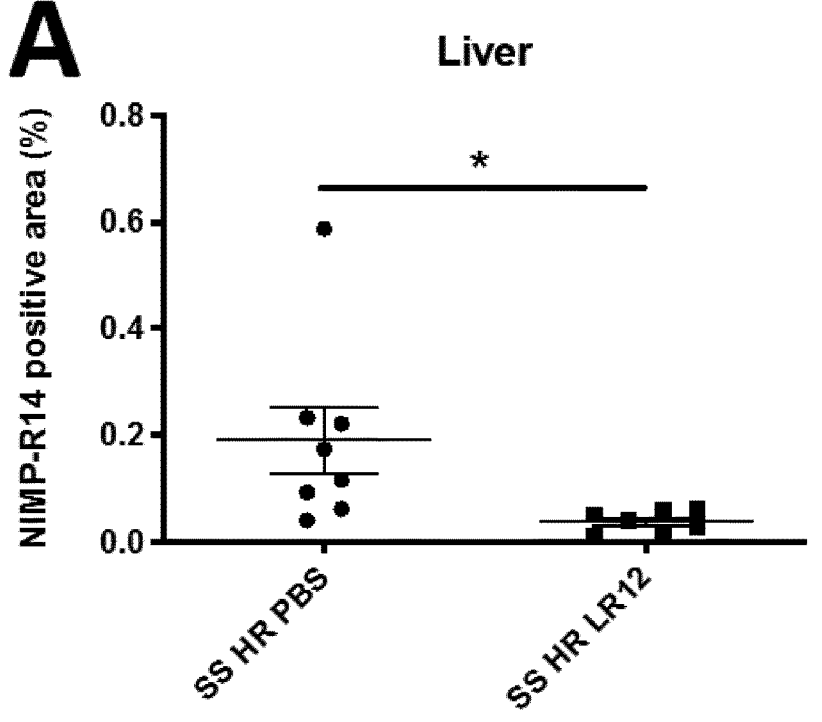
FIG. 4: LR12 administration induced a significant reduction in the abundance of neutrophils on histological sections of liver (A) and lung (B) from sickle cell mice. The amount of PMNs is expressed as % green fluorescent surface. * p<0.05, ** p<0.01. SS PBS (n=8), SS LR12 (n=7).
Figure 4B:
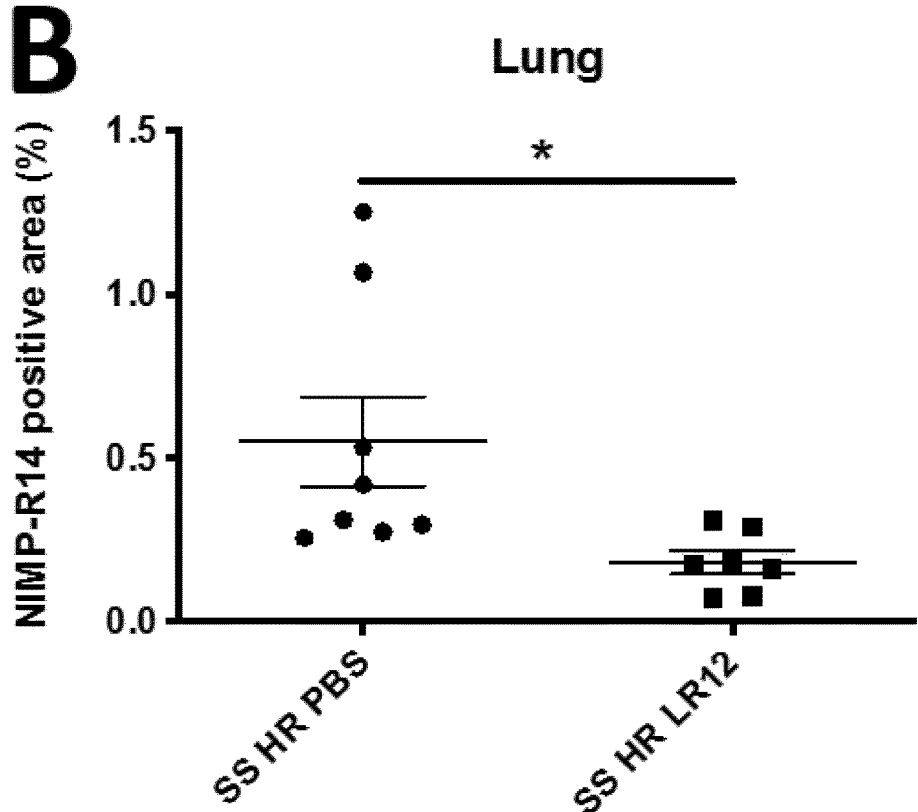
Figure 5:
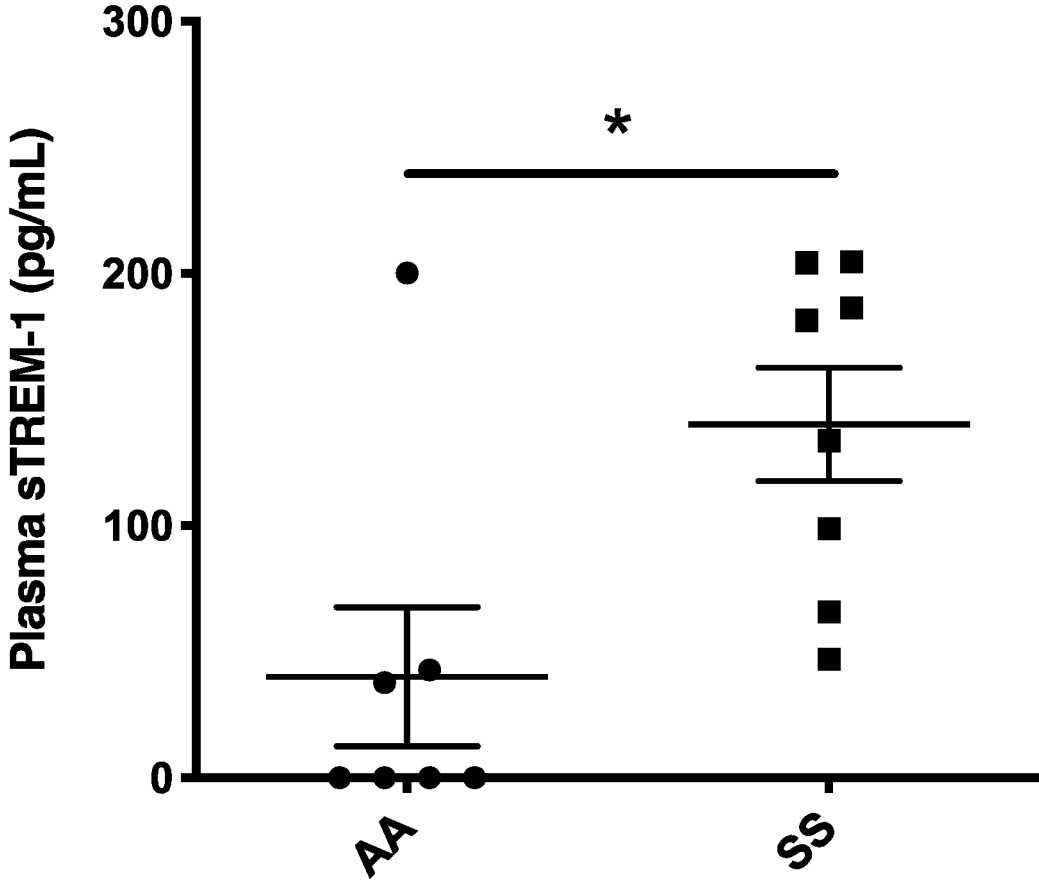
FIG. 5: Plasma concentrations of sTREM-1 are significantly higher in SS sickle cell mice than in mice carrying normal AA hemoglobin. *: p<0.05.

Results:

We showed that LR12 reduces the rolling, adhesion and transmigration of neutrophils in post-capillary venules after challenge with TNFα (FIGS. 1A-1C). Likewise, genetic deletion of Trem-1 did not decrease rolling, but decreases the adhesion and transmigration of neutrophils after challenge with TNFα (FIGS. 2A-2C). LR12 administration promoted a significant reduction vascular congestion of tissues of sickle cell mice (FIGS. 3A-3D). LR12 administration induced a significant reduction in the abundance of neutrophils in tissues of sickle cell mice during experimental vaso-occlusive crisis (VOC) (FIGS. 4A and 4B). Plasma concentrations of sTREM-1 are significantly higher in SS sickle cell mice than in mice carrying normal AA hemoglobin (FIG. 5).

REFERENCES

Throughout this application, various references describe the state of the art to which this invention pertains. The disclosures of these references are hereby incorporated by reference into the present disclosure.

The invention claimed is:

1. A method of treating a vaso-occlusion in a patient having sickle cell disease comprising administering to the patient a therapeutically effective amount of a TREM-1 inhibitor, wherein the TREM-1 inhibitor is a peptide selected from the group consisting of SEQ ID NO:2, SEQ ID NO: 3; SEQ ID NO:4, SEQ ID NO:5, SEQ ID NO:6, SEQ ID NO:7, SEQ ID NO: 8, SEQ ID NO:9, SEQ ID NO: 10 and SEQ ID NO:11.

* * * * *